United States Patent
Shimizu et al.

(10) Patent No.: US 9,417,104 B2
(45) Date of Patent: Aug. 16, 2016

(54) ELECTRONIC GASTROINTESTINAL SCREENING

(75) Inventors: Jeff Shimizu, Cortlandt Manor, NY (US); Karen Trovato, Putnam Valley, NY (US)

(73) Assignee: Medimetrics Personalized Drug Delivery B.V., Eindhoven (NL)

( * ) Notice: Subject to any disclaimer, the term of this patent is extended or adjusted under 35 U.S.C. 154(b) by 1374 days.

(21) Appl. No.: 12/096,374

(22) PCT Filed: Dec. 5, 2006

(86) PCT No.: PCT/IB2006/054610
§ 371 (c)(1),
(2), (4) Date: Jun. 6, 2008

(87) PCT Pub. No.: WO2007/066288
PCT Pub. Date: Jun. 14, 2007

(65) Prior Publication Data
US 2008/0262313 A1 Oct. 23, 2008

Related U.S. Application Data
(60) Provisional application No. 60/748,304, filed on Dec. 7, 2005.

(51) Int. Cl.
| | | |
|---|---|---|
| A61B 1/06 | (2006.01) | |
| G01D 9/00 | (2006.01) | |
| A61B 1/04 | (2006.01) | |
| A61B 5/145 | (2006.01) | |

(Continued)

(52) U.S. Cl.
CPC ............ *G01D 9/005* (2013.01); *A61B 1/041* (2013.01); *A61B 5/14539* (2013.01); *A61B 5/42* (2013.01); *A61B 1/273* (2013.01); *A61B 5/0059* (2013.01); *A61B 5/01* (2013.01)

(58) Field of Classification Search
USPC .................. 600/103, 109, 117–118, 160, 302
See application file for complete search history.

(56) References Cited

U.S. PATENT DOCUMENTS

| | | | | |
|---|---|---|---|---|
| 5,353,807 A | * | 10/1994 | DeMarco | A61B 1/00078 128/899 |
| 5,833,603 A | * | 11/1998 | Kovacs et al. | 600/317 |

(Continued)

FOREIGN PATENT DOCUMENTS

| | | |
|---|---|---|
| JP | H10101965 | 4/1998 |
| JP | 2004261522 | 9/2004 |

(Continued)

OTHER PUBLICATIONS

The European Office Action mailed Dec. 18, 2013 for European patent application No. 06832096.9, a counterpart foreign application of U.S. Appl. No. 12/096,374, 5 pages.

(Continued)

*Primary Examiner* — Anhtuan T Nguyen
*Assistant Examiner* — Jae Woo
(74) *Attorney, Agent, or Firm* — Lee & Hayes, PLLC (57) ABSTRACT

Gastrointestinal screening includes disposing a self-contained electronic capsule in a gastrointestinal tract. The electronic capsule is adapted to acquire data that is responsive to one or more physical conditions in the gastrointestinal tract and to compare the acquired data with stored threshold data to generate a discrete output relating to the condition of the gastrointestinal tract.

20 Claims, 9 Drawing Sheets (51) Int. Cl.
*A61B 1/273* (2006.01)
*A61B 5/00* (2006.01)
*A61B 5/01* (2006.01)

(56) References Cited

U.S. PATENT DOCUMENTS

| | | | |
|---|---|---|---|
| 6,240,312 B1 | 5/2001 | Alfano et al. | |
| 6,324,418 B1* | 11/2001 | Crowley | A61B 5/0031 600/179 |
| 2001/0051766 A1 | 12/2001 | Gazdzinski | |
| 2002/0198470 A1* | 12/2002 | Imran | A61M 31/002 600/587 |
| 2003/0167000 A1* | 9/2003 | Mullick et al. | 600/424 |
| 2003/0216622 A1* | 11/2003 | Meron | A61B 1/00147 600/300 |
| 2004/0162501 A1* | 8/2004 | Imran | 600/547 |
| 2004/0175289 A1* | 9/2004 | Takizawa | A61B 1/041 422/20 |
| 2004/0176685 A1 | 9/2004 | Takizawa et al. | |
| 2004/0225188 A1* | 11/2004 | Kleen et al. | 600/159 |
| 2004/0249245 A1* | 12/2004 | Irion | 600/160 |
| 2005/0043587 A1* | 2/2005 | Fujimori et al. | 600/160 |
| 2005/0137468 A1* | 6/2005 | Avron et al. | 600/310 |
| 2005/0148847 A1* | 7/2005 | Uchiyama et al. | 600/407 |
| 2005/0158246 A1* | 7/2005 | Takizawa et al. | 424/10.1 |
| 2005/0177069 A1* | 8/2005 | Takizawa et al. | 600/573 |
| 2005/0192478 A1* | 9/2005 | Williams | B82Y 10/00 600/160 |
| 2005/0288594 A1* | 12/2005 | Lewkowicz et al. | 600/478 |
| 2007/0156015 A1* | 7/2007 | Gilad | A61B 1/00156 600/102 |
| 2008/0055404 A9* | 3/2008 | Glukhovsky et al. | 348/77 |
| 2011/0060189 A1* | 3/2011 | Belson | 600/117 |

FOREIGN PATENT DOCUMENTS

| | | |
|---|---|---|
| JP | 200566096 | 3/2005 |
| WO | 02/36007 A1 | 5/2002 |
| WO | WO2005058129 | 6/2005 |
| WO | WO2006077530 | 7/2006 |

OTHER PUBLICATIONS

Translated Japanese Office Action mailed Nov. 12, 2013 for Japanese patent application No. 2008543972, a counterpart foreign application of U.S. Appl. No. 12/096,374, 4 pages.

Translated Japanese Office Action mailed Jun. 2, 2015 for Japanese patent application No. 2008-543972, a counterpart foreign application of U.S. Appl. No. 12/096,374, 8 pages.

Final Office Action for U.S. Appl. No. 12/096,374, mailed on Jan. 30, 2015, Jeff Shimizu, "Electronic Gastrointestinal Screening", 11 pages.

* cited by examiner

ELECTRONIC GASTROINTESTINAL SCREENING

BACKGROUND AND SUMMARY

This invention relates to detection of gastrointestinal conditions. More particularly, this invention relates to gastrointestinal screening that can be carried out by persons lacking medical training, such as by ordinary patients, to determine whether gastrointestinal conditions exist that warrant further investigation by trained medical personnel.

Many technologies exist for obtaining information regarding a person's gastrointestinal tract using an instrument disposed within the person's gastrointestinal tract. For instance, endoscopy may be performed to enable a medically trained person to examine a patient's gastrointestinal tract visually for conditions of interest such as cancerous or pre-cancerous tissues, bleeding, or infection. The American Cancer Society recommends that anyone over the age of fifty undergo routine colonoscopy for the screening of colorectal cancer every ten years, or flexible sigmoidoscopy every five years. There may be no other indication for these procedures.

Colonoscopy and sigmoidoscopy have drawbacks and limitations. They are relatively costly, requiring appropriate patient preparation and the time of a doctor to perform them. They are often regarded as uncomfortable and embarrassing. They may require some level of anaesthesia, which has associated risks. Additional risks such as bowel perforation are associated with the procedures themselves. They are performed in a doctor's office or hospital, which lacks privacy and convenience. They do not reach the small intestine, where inflammation, bleeding, and cancer can occur.

To address some of the drawbacks and limitations of colonoscopy and sigmoidoscopy, so-called "capsule endoscopes" have been developed. These are self-contained devices that are small enough to pass through the gastrointestinal tract, and contain apparatus to acquire image data for diagnostic purposes as they do so. For example, Given Imaging Ltd. of Yoqneam, Israel markets a device under the trademark "PillCam" that can be swallowed; as it passes through the digestive system, it acquires video images and transmits video data to a data recorder worn by the patient for storage and later review by a physician for diagnosis. Such capsules are, at present, fairly expensive single-use devices. Interpretation of the recorded capsule endoscopy data by a physician may require on the order of an hour.

Various self-contained diagnostic data acquisition devices that can be swallowed and pass through the gastrointestinal tract are disclosed in U.S. Pat. No. 6,240,312 to Alfano et al. and in U.S. Patent Application Publication US2001/0051766A1 to Gazdzinski. Such devices are intended to enable a physician to make a diagnosis, and require a medically trained person to review the acquired data for that purpose.

Screening tests may be used to help determine which patients should receive diagnostic procedures. Desirable properties of such a screening test typically include a cost that is lower than the cost of the diagnostic procedure being screened for, and the ability to be administered by someone without the medical training required for the diagnostic procedure being screened for, particularly by the patient being screened. For instance, as a screening test to help determine if a colonoscopy or sigmoidoscopy should be performed, a patient can perform a Fecal Occult Blood Test (FOBT) or Fecal Immunochemical Test (FIT) to analyze the patient's stool for the presence of blood. Such blood-in-stool tests are relatively inexpensive and do not require a medically trained person, but they have drawbacks. For instance, some gastrointestinal conditions of interest, such as certain tumors, do not cause blood in the stool. Other conditions for which diagnostic tests need not be performed, such as hemorrhoids, may cause blood in the stool that results in a positive FOBT or FIT. Although a FOBT or FIT may indicate the presence of blood, it does not indicate the location in the gastrointestinal tract of the blood source. FOBT and FIT generally have poor sensitivity and specificity.

Screening the population with a simple procedure that can be performed privately outside the doctor's office could reduce the number of sigmoidoscopy and colonoscopy procedures performed, and provide significant savings to the healthcare system. It would be desirable to have a gastrointestinal screening test that is relatively inexpensive, that can be administered by a person without medical training, such as a patient, and that provides an output that correlates well with the appropriateness of diagnostic testing. The present invention provides electronic capsules for gastrointestinal screening, and methods of gastrointestinal screening using such electronic capsules.

Gastrointestinal screening in accordance with the present invention includes disposing a self-contained electronic capsule in a gastrointestinal tract. Embodiments of the invention include an electronic capsule that is adapted to acquire data that is responsive to one or more physical conditions in the gastrointestinal tract and to compare the acquired data with stored threshold data in order to generate a discrete output relating to the condition of the gastrointestinal tract. Other features and aspects of the present invention may be understood with reference to the following description, the claims, and the drawing.

DETAILED DESCRIPTION

In the following discussion and in the drawings, reference numerals with letter suffixes refer to a particular instance or example of items that may be referred to generally or collectively by the same reference numeral without such suffix.

Figure 1:
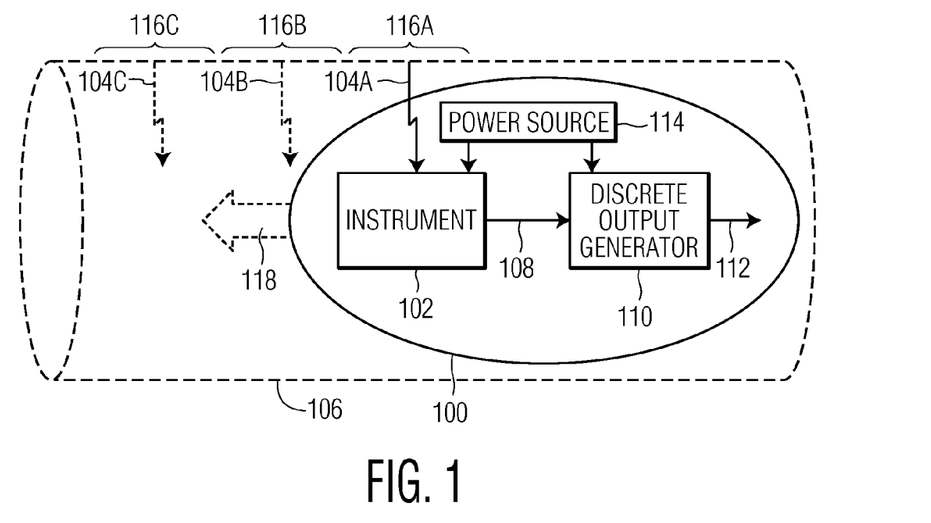
FIG. 1 is a schematic diagram illustrating certain features of an electronic capsule in accordance with the present invention.

FIG. 1 illustrates, by dotted lines, a section of a gastrointestinal tract 106, such as an intestine. Disposed within gastrointestinal tract 106 is a capsule 100 that contains apparatus suitable for performing gastrointestinal screening. Capsule 100 includes an instrument 102 and a discrete output generator 110. Capsule 100 also includes a power source 114, such as a battery, for providing operating power. Capsule 100 may also include a microprocessor or microcontroller, not shown, to control operation of the capsule or parts thereof as described herein.

Instrument 102 is responsive to physical conditions 104 in the surrounding region; the conditions to which instrument 102 responds are selected to be indicative of gastrointestinal conditions of interest. An example of a type of physical condition to which instrument 102 may be responsive is light, such as may be generated by tissue fluorescence or reflection, and a light-responsive system will be described later in connection with FIG. 8. In general, however, instrument 102 may be responsive to any physical condition or conditions, including electrical, magnetic, electromagnetic, chemical, thermal, and/or mechanical conditions, that are associated with or may be used in the process of determining a gastrointestinal condition of interest.

Capsule 100 moves through gastrointestinal tract 106 in the direction indicated by arrow 118 in FIG. 1; such movement may be caused, for instance, by peristalsis. Instrument 102 acquires data relating to the condition of the gastrointestinal tract in the region 116 adjacent 100 by responding to physical conditions 104 at that location. For instance, when capsule 100 is adjacent location 116A, instrument 102 responds to physical conditions 104A and acquires data that relates to the condition of the gastrointestinal tract at location 116A; at a later time, when capsule 100 has moved and is adjacent location 116B, instrument 102 responds to physical conditions 104B and acquires data that relates to the condition of the gastrointestinal tract at location 116B.

Instrument 102 receives physical conditions 104 and provides, as instrument output 108, a discrete electrical signal that is responsive to physical conditions 104. As used herein, a discrete signal is a signal whose state is one of a finite number of predetermined possible states. In the simplest case, the discrete electrical signal of instrument output 108 is binary; that is, it can assume one of two possible states (for example, high or low, on or off) based on the acquired data. However, instrument 102 may provide more that two possible states for instrument output 108. The states that instrument output 108 may assume, and the physical conditions 104 that correspond to those states, are selected to provide desired information in a screening test. For example, one state of instrument output 108 may correspond to conditions of the gastrointestinal tract adjacent capsule 100 that are considered to be "normal," and another state of instrument output 108 may correspond to conditions of the gastrointestinal tract adjacent capsule 100 that are considered to be "abnormal."

Discrete output generator 110 receives instrument output 108 and provides, as an output of capsule 100 representing results of a screening test, discrete output 112, the state of which is based on the state of instrument output 108. For example, one state of discrete output 112 may represent that conditions of the gastrointestinal tract that are considered "abnormal" were detected during a screening test and that a diagnostic test should be performed, and another state of discrete output 108 may represent that "abnormal" conditions of the gastrointestinal tract were not detected during a screening test and that a diagnostic test need not be performed. At least one possible state of discrete output 112 is a state of capsule 100, or caused by capsule 100, that is different from the state prior to, or in the absence of, administering a screening test using capsule 100.

Discrete output 112 may include a human-perceptible output, which facilitates unaided use by a person in determining results of a screening test. A human-perceptible discrete output 112 may include a visually perceptible output.

For example, such a visually perceptible output may include a color output. Capsule 100 may have a region that has a first color prior to administering a screening test, and is caused to have a second color different from the first color if, during a screening test, capsule 100 is exposed to physical conditions 104 corresponding to gastrointestinal conditions indicating that a diagnostic test should be performed. The color change may be effected by opening a hatch in response to instrument output 108 and releasing a substance into an externally visible indicator region of capsule 100. The substance may be colored matter such as ink, dye, or pigment, or a substance that causes a color-changing chemical reaction in the indicator region. Alternatively, discrete output generator 110 may open an external hatch in response to instrument output 108 and release colored matter into the region surrounding the capsule. Such colored matter may be observable in the toilet when capsule 100 is excreted, for instance, by coloring the water in the toilet.

A visually perceptible discrete output 112 may include a light output. For example, discrete output generator 110 may contain a lamp, such as a light-emitting diode (LED), the illumination state of which is controlled by instrument output 108. For instance, an LED may be lit or flashed to indicate that during a screening test, capsule 100 was exposed to physical conditions 104 corresponding to gastrointestinal conditions indicating that a diagnostic test should be performed.

A human-perceptible discrete output 112 may include an audible output. For example, discrete visual output generator 110 may include an electroacoustic transducer that generates a tone or other acoustic signal to indicate that during a screening test, capsule 100 was exposed to physical conditions 104 corresponding to gastrointestinal conditions indicating that a diagnostic test should be performed.

Discrete output 112 may include a wireless output, such as a radio or infrared output. For instance, the presence of a radio or infrared output may indicate that during a screening test, capsule 100 was exposed to physical conditions 104 corresponding to gastrointestinal conditions indicating that a diagnostic test should be performed. Alternatively, a radio or infrared output may be modulated to represent states corresponding to the states of instrument output 108. A wireless output from capsule 100 may include, in addition to discrete state information, data acquired during a screening test. A wireless output from capsule 100 may be received by a local receiver that extracts, from the wireless output, the state information (e.g., whether the result of a screening test was "normal" or "abnormal") and any other data included. Such information and data may be stored in the local receiver and/or communicated over a network, for instance, to medical professionals.

Figure 2:
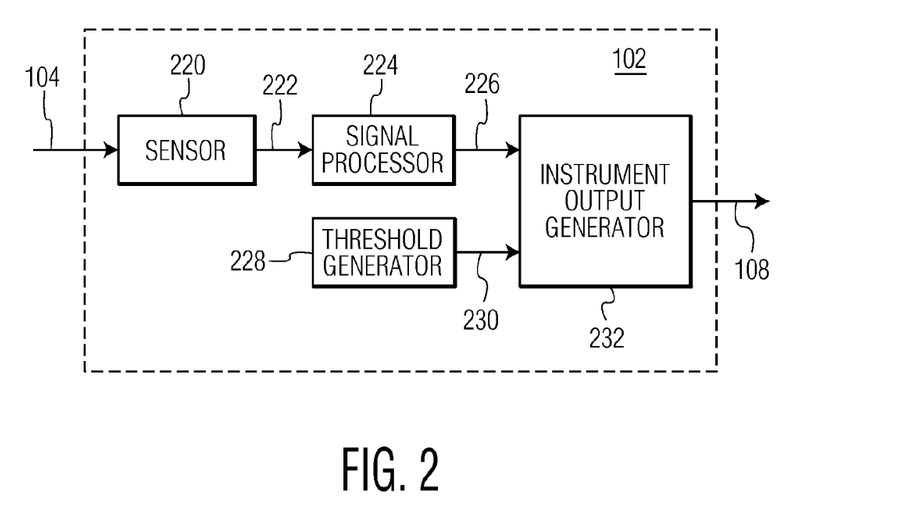
FIG. 2 is a schematic diagram illustrating an example of an instrument that may be used in the electronic capsule of FIG. 1.

FIG. 2 is a schematic diagram illustrating an example of an instrument that may be used in the electronic capsule of FIG. 1. As shown in FIG. 2, instrument 102 includes sensor 220 that is exposed to physical conditions 104 adjacent capsule 100 and generates an electrical output signal 222 that is responsive to those physical conditions. Signal processor 224 receives and processes sensor output signal 222 to provide an output signal representing acquired data 226 relating to the condition of the gastrointestinal tract based on physical conditions 104. Threshold generator 228 provides threshold data 230 that defines sets of possible values of acquired data 226. For instance, if acquired data 226 has a range of possible values, threshold data 230 may identify an intermediate value forming a boundary between a set comprising a range of values higher than the threshold value and a set comprising a range of values lower than the threshold value. Instrument output generator 232 receives and compares threshold data 230 and acquired data 226, and controls the state of instrument output 108 in accordance with which of the sets of values, as defined by threshold data 230, the acquired data falls in.

For example, in an instrument 102 designed to illuminate gastrointestinal tissue and detect inflammation by its redness, sensor 220 might be a photodetector that receives light reflected from gastrointestinal tissue adjacent capsule 100 and produces, as an output, a current that is proportional to the intensity of received light in red wavelengths. Signal processor 224 might perform current-to-voltage conversion and amplification, and generate an output voltage that is proportional to the photodetector current. Threshold generator 228 might generate an output voltage representing a threshold that divides the entire range of possible signal processor output voltages into two ranges: a range above the threshold, corresponding to sufficient redness that a diagnostic test of a person's gastrointestinal condition is warranted, and a range below the threshold, corresponding to insufficient redness to warrant a diagnostic test. Instrument output generator 232 might be a comparator having an input that receives the signal processor output voltage and an input that receives the threshold voltage, and that produces a discrete output whose high or low state is determined by which input is greater.

In the foregoing example, the signal processor output and the threshold data are analog signals, but the signal processor could also include analog-to-digital conversion, the threshold data could be digital data stored in a memory, and the instrument output generator could compare digital data values. In the foregoing example, the threshold data is a single value that divides the possible signal processor output into two ranges, each of which corresponds to one of the two possible instrument output states. However, the threshold data could also include multiple values, such as a pair of threshold values that divide the possible signal processor output into three ranges, a low range, a medium range, and a high range, each of which corresponds to one of the three possible instrument output states. In the foregoing example, a single acquired data signal derived from a single sensor is compared with a threshold value for acquired data, but acquired data signals might be generated from two or more sensors, and the instrument output generator might generate an output state that is a function of two or more acquired data signals, and threshold values might be generated defining states that are functions of two or more acquired data signals.

Figure 3:
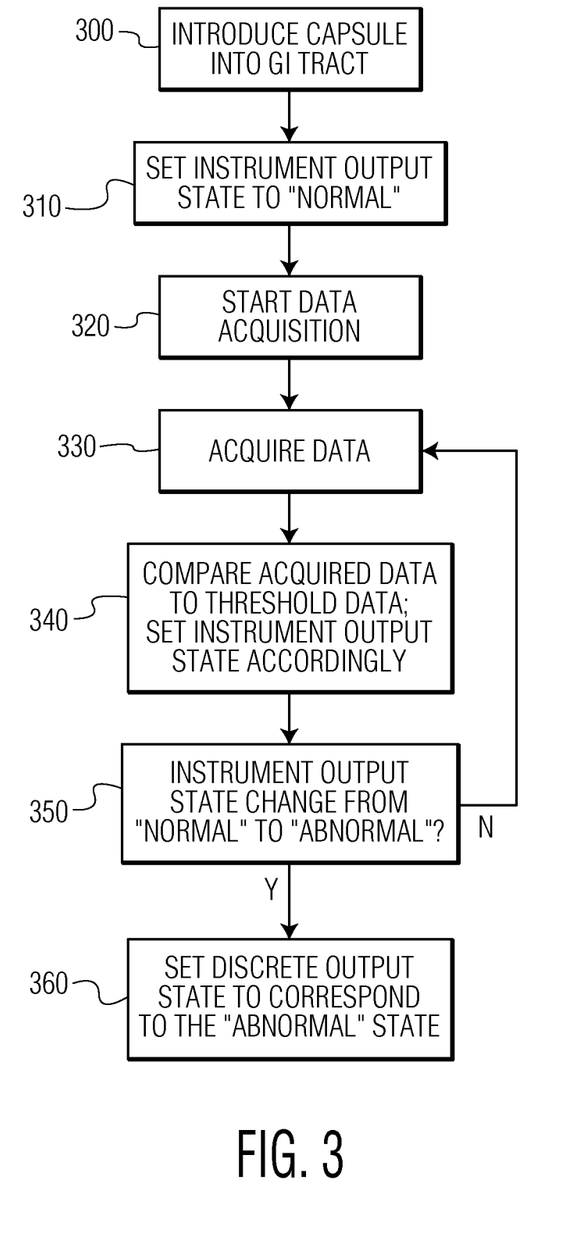
FIG. 3 is a flow diagram illustrating a first method of gastrointestinal screening in accordance with the present invention.

FIG. 3 is a flow diagram illustrating a first method of gastrointestinal screening in accordance with the present invention. In step 300, a capsule such as that of FIGS. 1 and 2 is introduced into a person's gastrointestinal tract, such as by swallowing. In step 310, the instrument is initialized by setting instrument output 108 to a state corresponding to a gastrointestinal condition that does not warrant administering a diagnostic test, which will be referred to as a "normal" state. Discrete output 112 will be in a corresponding "normal" state.

In step 320, data acquisition commences; this step may be triggered when capsule 100 enters an area in which screening activity is desired. For instance, the pH of the stomach is typically about 2-3, and the pH of the small intestine is typically above 6, and capsule 100 may include a pH-responsive instrument that detects such change and triggers the start of data acquisition when capsule 100 exits the stomach and enters the small intestine.

In step 330, data is acquired from the region adjacent capsule 100, for instance, from location 116A illustrated in FIG. 1, by sensor 220 providing a signal that is responsive to physical conditions in that region and signal processor 224 processing such signal to produce acquired data 226. In step 340, acquired data 226 is compared with threshold data 230; the state of instrument output 108 is set based on the results of the comparison.

The state of instrument output 108 is monitored in step 350. If its state (which was initialized to a "normal" state in step 310) has not changed, then the state of discrete output 112 is not changed. Capsule 100 moves through gastrointestinal tract 106 in the direction of arrow 118 by peristalsis, the process loops to step 330, and data is acquired from a successive location 116B. If at some location in gastrointestinal tract 106 it is determined in step 350 that instrument output 108 has changed and is in an "abnormal" state, in step 360 discrete output generator 110 sets the state of discrete output 112 to a corresponding "abnormal" state. As has been described, such a discrete output state may include a lamp illumination state or a state of release of colored material within or external to capsule 100, for instance. In the method illustrated in FIG. 3, the "abnormal" state of discrete output 112 is triggered upon the occurrence of an "abnormal" state in instrument output 108.

Figure 4:
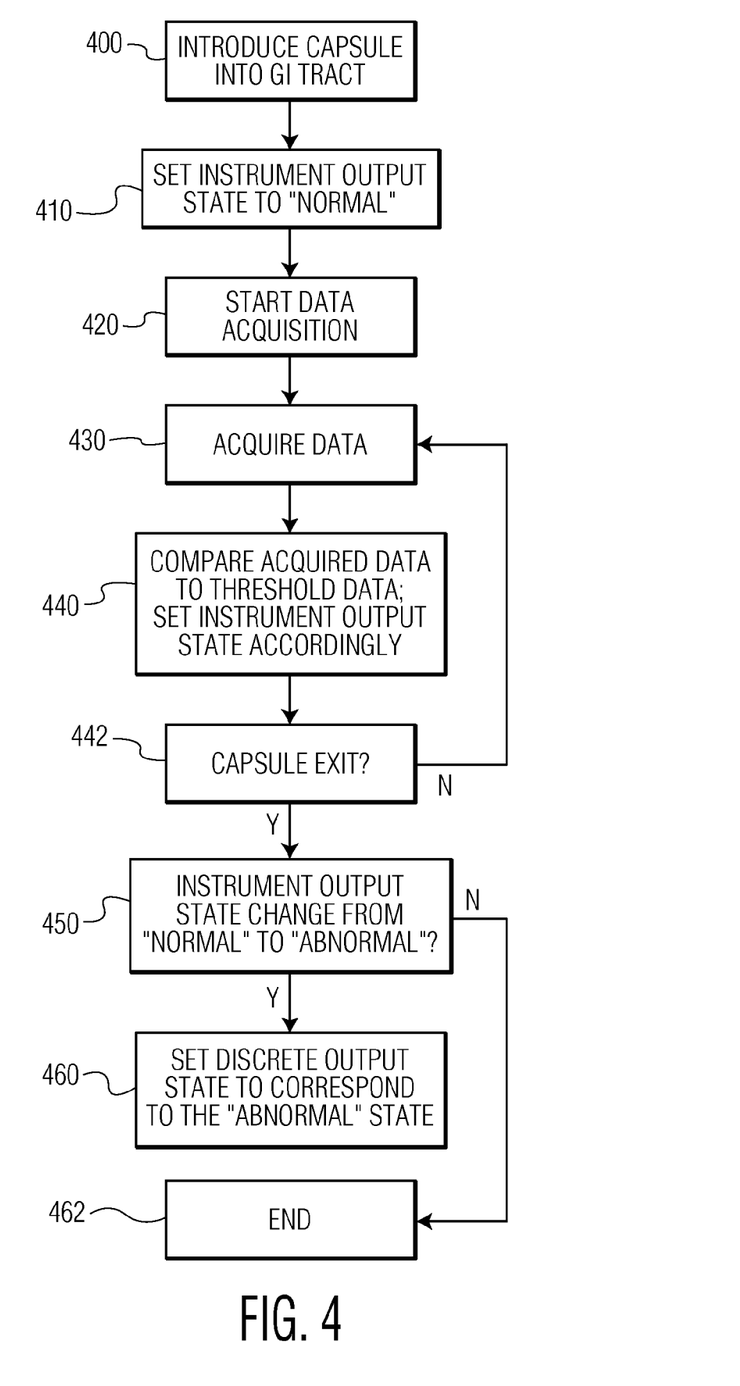
FIG. 4 is a flow diagram illustrating a second method of gastrointestinal screening in accordance with the present invention.

FIG. 4 is a flow diagram illustrating a second method of gastrointestinal screening in accordance with the present invention. Steps 400-440 are analogous to steps 300-340 previously described. In step 442, a determination is made as to whether capsule 100 has exited the gastrointestinal tract; if not, monitoring by data acquisition and threshold comparison continues. If in step 442 it is determined that capsule 100 has exited the gastrointestinal tract, and if in step 450 it is determined that instrument output 108 changed to an "abnormal" state during the data acquisition process, then in step 460 discrete output 112 is set to its "abnormal" state. If in step 450 it is determined that instrument output 108 did not change to an "abnormal" state during the data acquisition process, then the process ends in step 462. The capsule's exit from the gastrointestinal tract may be determined in a variety of ways. For instance, capsule 100 might include a photodetector adapted to detect an increase in light level, a pH detector adapted to detect a change in pH, or a temperature detector adapted to detect a change in temperature as the capsule exits the body and enters the water in a toilet.

Delaying the generation of a discrete output until capsule 100 has exited the gastrointestinal tract, as illustrated in FIG. 4, may be beneficial for a variety of reasons. It may save power; for instance, if the discrete output includes an illuminated lamp, illuminating that lamp while the capsule is in the gastrointestinal tract would consume power with little benefit, and delaying illumination until after the capsule exits the body and can be seen would reduce the capacity requirements for power source 114. Delaying the generation of a visually perceptible output until capsule 100 has exited the gastrointestinal tract may also enable the visually perceptible output to be more easily perceived. For instance, if the visually perceptible output includes a release of colored matter from capsule 100 to its external surroundings, so as to be visible in the water in a toilet when excreted, a given amount of colored matter may provide a more easily discerned indication if released when capsule 100 is in the toilet.

Figure 5:
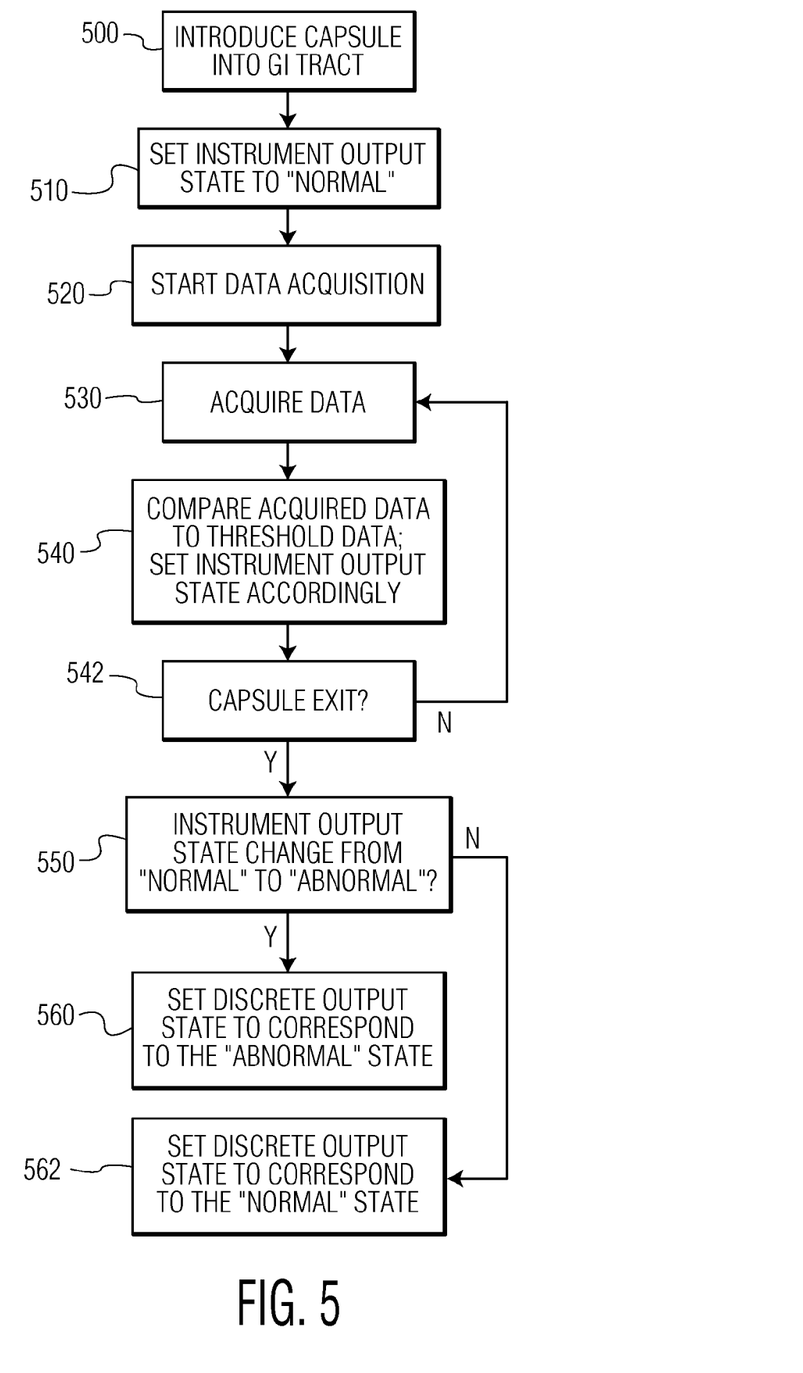
FIG. 5 is a flow diagram illustrating a third method of gastrointestinal screening in accordance with the present invention.

FIG. 5 is a flow diagram illustrating a third method of gastrointestinal screening in accordance with the present invention. Steps 500-550 are analogous to steps 400-450 previously described. The method of FIG. 5 includes an aspect that fosters confidence in the results of the screening test. If the discrete output corresponding to a "normal" screening test is the same as the state prior to administering a test, for instance, an unlit lamp or no color change, then the existence of that state after a capsule has passed through a gastrointestinal tract is ambiguous. It might be due to a successfully completed screening test that produced a "normal" result, or it might be due to a failure of the capsule. In order to avoid such ambiguity, discrete output generator 110 provides at least two states of discrete output 112, each of which differs from the output state prior to administering a test, and the method of FIG. 5 includes setting the discrete output state to one of those states in response to the state of instrument output 108. For instance, for a lamp output, a steadily lit LED might correspond to a "normal" state, and a flashing LED or a steadily lit LED of different color might correspond to an "abnormal" state, each of such states being distinguishable from an unlit lamp. For an output provided by a release of colored matter, release of material of a first color might correspond to a "normal" state, and release of material of a second color might correspond to an "abnormal" state, each of such states being distinguishable from the color state that would exist in the absence of a test (that is, the color state of the capsule without colored matter released within the capsule, or the color state of water in the toilet upon excretion without colored matter released outside the capsule).

Figure 6:
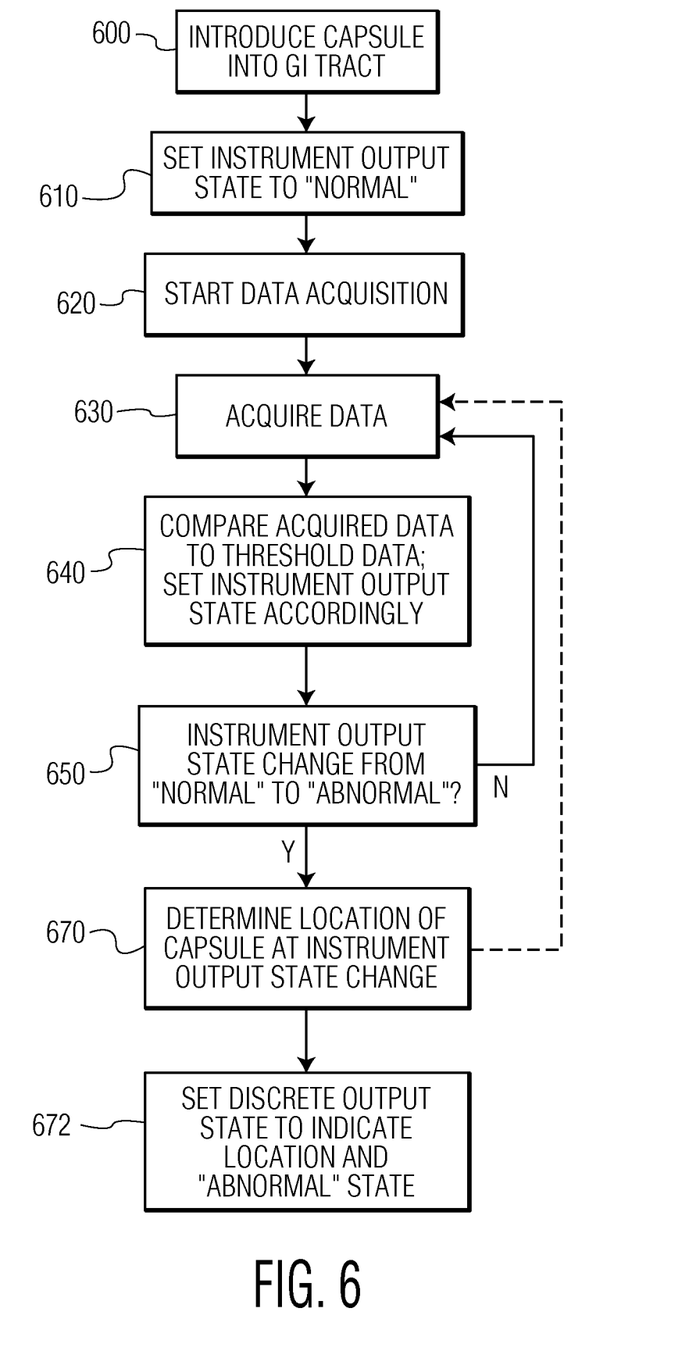
FIG. 6 is a flow diagram illustrating a fourth method of gastrointestinal screening in accordance with the present invention.

FIG. 6 is a flow diagram illustrating a fourth method of gastrointestinal screening in accordance with the present invention. Steps 600-650 are analogous to steps 300-350 previously described. In step 670, upon a change in instrument output 108 to an "abnormal" state, the location of capsule 100 is determined. For instance, pH may be detected by the electronic capsule, and the time elapsed after a pH change has occurred that indicates that the capsule has exited from the stomach, or the pH itself, may provide an approximate indication of the location of the capsule. In step 672 the state of discrete output 112 is set to indicate both the existence of an "abnormal" condition and the location where the "abnormal" condition was detected. Such location information can be used when performing a diagnostic test to identify an area that should be focused on. Various discrete outputs may indicate both the existence and location of a detected "abnormal" state. For instance, an LED may flash to indicate an "abnormal" state, and the flash pattern, such as the flash rate or the number of flashes in a repeated series, may indicate the location where the "abnormal" state was detected. If the discrete output is a release of colored matter, different colors may be released to indicate the location where the "abnormal" state was detected. For instance, releasing a first color may indicate an "abnormal" state in a first section of an intestine, a second color may indicate an "abnormal" state in a second section of the intestine, and so forth.

Figure 7:
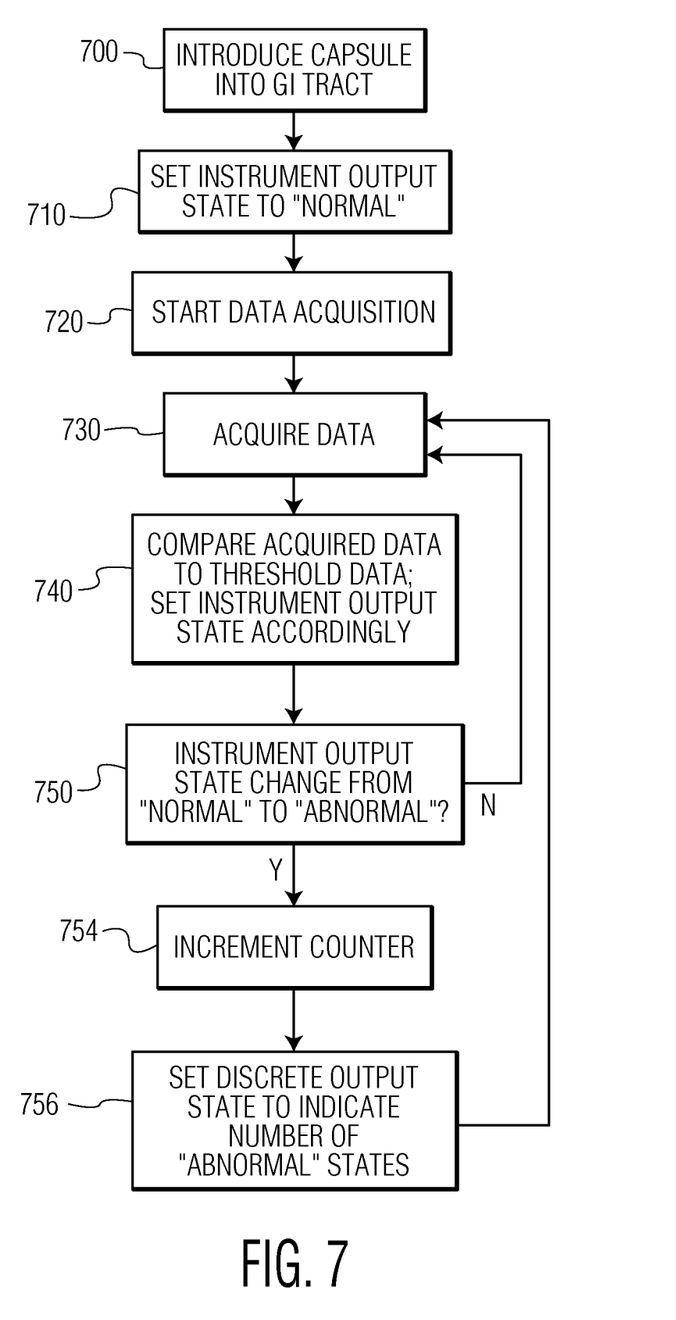
FIG. 7 is a flow diagram illustrating a fifth method of gastrointestinal screening in accordance with the present invention.

FIG. 7 is a flow diagram illustrating a fifth method of gastrointestinal screening in accordance with the present invention. It may be sufficient in some circumstances for a screening test to indicate only whether a condition has been detected that warrants a diagnostic test. However, in other circumstances, it may be desired to have a screening test using an electronic capsule that indicates the number of "abnormal" areas that were detected during the test. FIG. 7 illustrates such a test method. Steps 700-750 are analogous to steps 300-350 previously described. In the method of FIG. 7, if in step 750 capsule 100 has moved adjacent a location 116A where acquired data 104A causes a state change of instrument output 108 from "normal" to "abnormal," a counter that accumulates the number of such events is incremented in step 754. In step 756 the state of discrete output 112 is set to indicate the number of "abnormal" events indicated in the counter, and the process returns to step 730 and further data is acquired as capsule 100 passes through the gastrointestinal tract. For instance, when capsule 100 moves adjacent location 116B, if acquired data 104B indicates a "normal" state, then instrument output 108 will have a corresponding "normal" state. When capsule 100 moves adjacent location 116C, if acquired data 104C indicates an "abnormal" state, then instrument output 108 will again change its state to "abnormal", and the counter will be incremented in step 754 to reflect that state change. The state of discrete output 112 indicating the number of "abnormal" locations encountered by capsule 100, as contained in the counter, may for example comprise an LED that is periodically flashed that number of times. Such an output may be delayed until capsule 100 has exited the gastrointestinal tract, as described with respect to FIG. 4.

The foregoing discussion of the methods of FIGS. 3-7 has, for simplicity, been in terms of a capsule in which threshold data 230 divides the range of possible values of acquired data 226 into two sets: one set contains values that are considered not to warrant diagnostic testing and are therefore considered "normal", and the other contains values that are considered to warrant diagnostic testing and are therefore considered "abnormal." However, as was noted in the discussion of FIGS. 1 and 2, instrument output 108 and discrete output 112 may have more than two possible states. For example, threshold data 230 may divide the possible range of acquired data 226 into a larger number of sets representing a scale of increasing magnitude of the monitored condition, such as a scale of one to ten, and discrete output 112 may identify where on such a scale acquired data 226 falls. Such a system may provide several benefits. For instance, an output of nine on a screening test may cause a patient or physician to respond more quickly and investigate more thoroughly that an output of three would. Also, a change in screening test results may have substantial clinical significance, and a capsule providing a numerical score of a screening test would enable the scores of screening tests conducted at various times to be compared in order to detect changes. Accordingly, the methods of the present invention include those in which the discrete outputs have three or more states.

Figure 8:
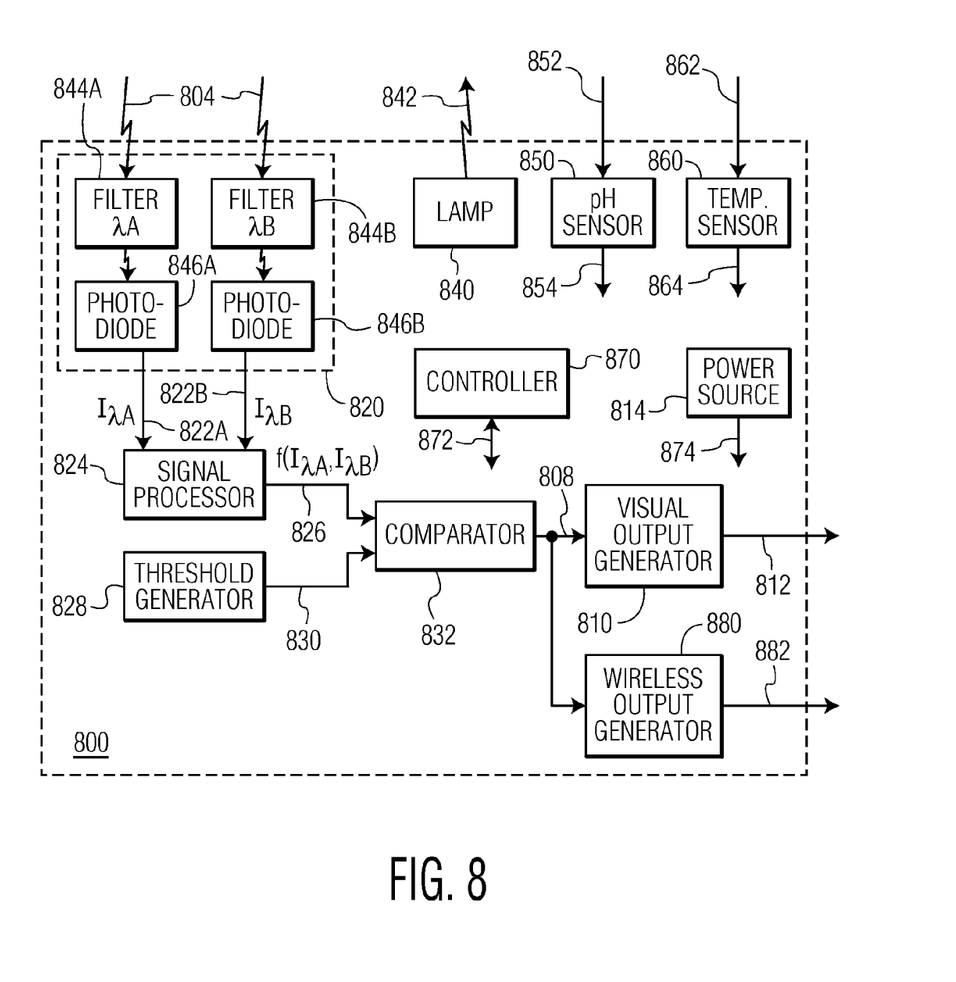
FIG. 8 is a schematic diagram illustrating certain features of an example of a light-responsive electronic capsule in accordance with the present invention.

FIG. 8 is a schematic diagram illustrating certain features of a light-responsive electronic capsule in accordance with the present invention. Capsule 800 is a more specific example of a capsule of the type that is shown generally in FIG. 1.

Capsule 800 includes a lamp 840 that emits light 842 so as to illuminate a portion of gastrointestinal tract adjacent capsule 800. Light 804 emanating from the area illuminated by lamp 840 is received by sensor 820. Sensor 820 includes two photodiodes, 846A and 846B, and two filters, 844A and 844B. Filter 844A permits light in a first set of wavelengths $\lambda A$ to reach photodiode 846A, and filter 844B permits light in a second set of wavelengths $\lambda B$ to reach photodiode 846B. Each photodiode 846 provides an output signal 822 having a value I that is a function of the light intensity in the part of the spectrum $\lambda$ that is passed by its associated filter 844. Thus sensor 820 comprises a spectrometer that is adapted to measure the intensities of spectral components of input light.

The photodiode outputs 826A and 826B, having values $I_{\lambda A}$ and $I_{\lambda B}$, are supplied as inputs to signal processor 824. Signal processor 824 produces an output 826 having a value that is a function of the input intensity values, i.e., $f(I_{\lambda A}, I_{\lambda B})$.

An example of a type of screening test that may be performed by light-responsive capsule 800 is a test based on tissue fluorescence. All tissue exhibits fluorescence when excited with ultraviolet (UV) or blue light. Such fluorescence that occurs without the introduction of an external agent is called autofluorescence. Studies of many forms of epithelial cancer, including cancer of the lung, breast, esophagus, ear/nose/throat, colon, bladder, and cervix, have correlated a change in autofluorescence with the presence of pre-cancerous or cancerous lesions. Standard endoscopic systems that use autofluorescence for cancer detection are commercially available.

Figure 9:
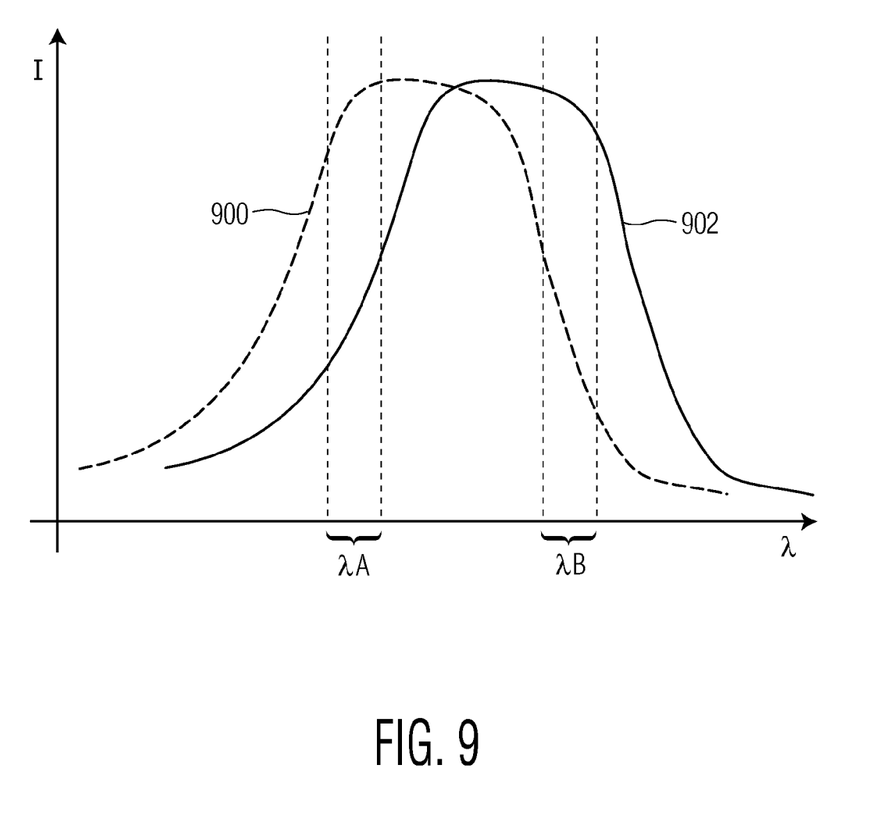
FIG. 9 is a graph illustrating autofluorescence spectral characteristics that might occur in normal and in cancerous tissue.

FIG. 9 is a graph of intensity I versus wavelength λ, schematically illustrating autofluorescence spectral characteristics that might occur in normal tissue and in cancerous tissue. Curve 900 illustrates a spectrum for normal tissue, and curve 902 illustrates a spectrum for cancerous tissue. Such spectra exhibit a peak, the wavelength of which shifts redward as tissue changes from normal to cancerous. Distinguishing autofluorescence spectral characteristics of normal and cancerous tissue may be accomplished by measuring the autofluorescence intensity I in selected wavelength ranges λA and λB.

For that purpose, capsule 800 may includes a lamp 840 that emits relatively short wavelength light effective to excite tissue autofluorescence, such as an LED that emits blue or UV light, and the passbands λA and λB of filters 844 may be as illustrated in FIG. 9. Signal processor 824 operates on intensity signals $I_{\lambda A}$ and $I_{\lambda B}$ to generate an output 826 that reflects autofluorescence characteristics and can be compared with threshold values 830 generated by threshold generator 828 to identify suspicious tissue.

For instance, $I_{\lambda A}-I_{\lambda B}$ is positive for curve 900 representing normal tissue and is negative for curve 902 representing cancerous tissue. Thus signal processor 824 may generate an output 826 that is a function of the intensity difference, i.e., $f(I_{\lambda A}-I_{\lambda B})$. Threshold generator 828 may generate a value of threshold data 830 that is intermediate the output 826 of signal processor 824 for normal and for cancerous tissues.

Also, $I_{\lambda A}/I_{\lambda B}$ is greater than one for curve 900 representing normal tissue and is less than one for curve 902 representing cancerous tissue. Thus signal processor 824 may generate an output that is a function of the intensity ratio, i.e., $f(I_{\lambda A}/I_{\lambda B})$. Threshold generator 828 may generate a value of threshold data 830 that is intermediate the output of signal processor 824 for normal and cancerous tissues. Other functions of the light intensity in differing wavelength ranges may also be used if such functions are capable of distinguishing normal tissue from abnormal tissue.

Threshold generator 828 may generate threshold data 830 that is the same in each capsule 100 that is intended to perform a particular type of screening test, such as for all cancer screening capsules. Alternatively, the threshold data 830 in a particular capsule may be generated in the course of performing a screening test. A person's gastrointestinal tract may be expected to contain primarily normal tissue, even if it also contains cancerous or pre-cancerous tissue. Autofluorescence data acquired during a screening test may be processed, such as by averaging or limit detection, to obtain a value that corresponds to the autofluorescence of the person's typical gastrointestinal tract tissue, and the threshold data used in the screening test (or in a part of a screening test) may be generated based on such processed data. For instance, threshold data 830 might be set by applying a multiplicative or additive offset to an average value of acquired data 826. Or, for simplicity, the apparatus might simply generate a binary instrument output 808 that is in one state if $I_{\lambda A}>I_{\lambda B}$ and in the other state if $I_{\lambda A}<I_{\lambda B}$, in which case the threshold data 830 would simply be a function of the current value of $I_{\lambda A}$ or $I_{\lambda B}$.

The apparatus of FIG. 8 may also be used to perform screening tests based on phenomena other than autofluorescence, and for conditions other than cancer. For instance, the presence of blood in the gastrointestinal tract, an "abnormal" condition that may be due to causes in addition to cancer, may be detected based on the differences in reflectance spectra of blood and normal tissue. Hemoglobin has a characteristic absorption spectrum with strong reflectance in the red, 600-800 nanometer wavelength region and absorption at shorter wavelengths. Normal tissue lacks such absorption. Spectral measurement of light 804 may, with appropriate selection of parameters such as the characteristics of filters 844, the processing applied by signal processor 824, and the values of threshold data 830, distinguish between the presence and absence of blood. Moreover, oxygenated and de-oxygenated hemoglobin have different absorption spectra, and the spectral measurements of capsule 800 may enable determination of the relative oxygenation of detected blood, providing additional diagnostic data.

Comparator 832 receives and compares threshold data 830 and acquired data 226, and controls the state of its output 808 based on the comparison to generate comparator output 808. A discrete output generator includes visual output generator 810, which receives comparator output 808 and provides visually perceptible output 812, and wireless output generator 880, which receives comparator output 808 and provides wireless output 882. Although both wireless output generator 880 and visual output generator 810 are shown, either may be used alone. The apparatus of FIG. 8 also includes power source 814 that provides power 874 to operate capsule 800.

FIG. 8 shows several additional components that optionally may be included in an electronic capsule according to the present invention. These include pH sensor 850 that is exposed to the contents 852 of the gastrointestinal tract adjacent capsule 800 and produces output 854 that is responsive to the pH of those contents. As has been described, such a pH-responsive output can be used to determine the location of capsule 800 within the gastrointestinal tract or its exit therefrom. FIG. 8 also shows a temperature sensor 860 that may be included, which receives thermal input 862 from the region of the gastrointestinal tract adjacent capsule 800 and produces output 854 that is responsive to the temperature there. Such a temperature-responsive output can be used to detect the exit of capsule 800 from the gastrointestinal tract, as has been described; it might also be used to detect abnormal gastrointestinal conditions such as inflammation.

Finally, FIG. 8 shows controller 870, which might be implemented using a microprocessor or microcontroller, for instance. Controller 870 may be used to control operation of capsule 800, including performing the methods described herein. In doing so, data 872 is received from and/or transmitted to other components of capsule 800 that interface with controller 870. A controller 870 may implement some or all of the functions that have been described with respect to other components of capsule 800.

The apparatus of FIG. 8 illustrates two photodiodes 846, each with its own filter 844. It should be understood that a spectrometer for use in such an apparatus may be made using many other configurations. For instance, other types of light detector may be used. A single light detector could be used, and the filtering of the light incident upon it could be sequentially changed to make the detector responsive to different wavelengths at different times, or an imaging light detector could be used. Light intensity in three or more wavelength ranges might be measured. Although threshold data 830 might represent an intensity threshold, it might also represent a threshold of other parameters. For instance, signal processor 824 might generate acquired data 826 representing which of a plurality of wavelength ranges contains the spectral peak of light 804, and threshold data 830 might represent one or more wavelength ranges in which a spectral peak corresponds to an "abnormal" gastrointestinal condition. A sensor having an array of photodetectors enables improved detection of abnormal areas of the gastrointestinal tract, compared to a single-photodetector sensor having the same field of view. An abnormal area occupying a small part of the field of view may provide a relatively easily detected signal in elements of a photodetector array that receive light only from that area; detection is more difficult when the light from the abnormal area is combined with the light from normal tissue in the field of view of a single photodetector. For the screening application of the present invention, a relatively small array (e.g., 16×16) may be adequate, whereas much larger arrays (e.g., 420×420) are used in diagnostic imaging applications.

Figure 10:
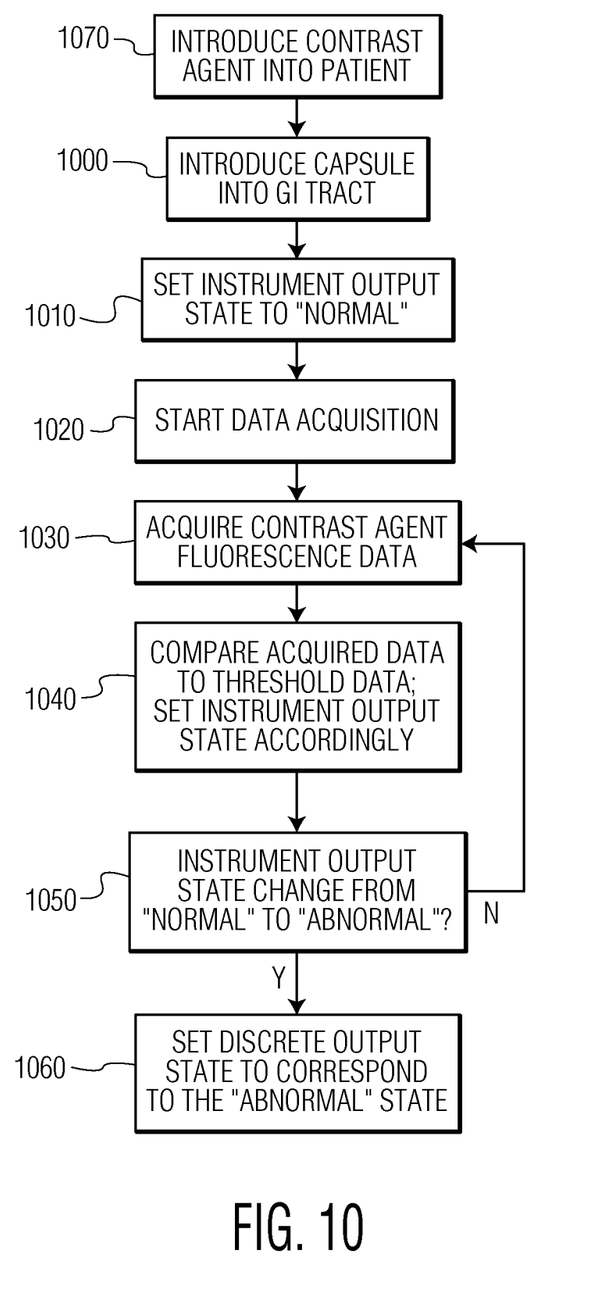
FIG. 10 is a flow diagram illustrating a sixth method of gastrointestinal screening in accordance with the present invention.

FIG. 10 is a flow diagram illustrating a sixth method of gastrointestinal screening in accordance with the present invention. The method uses a light-responsive capsule such as capsule 800, and measures fluorescence of a contrast agent. Although the method is illustrated as a variation of the method of FIG. 3, it can also be applied to the other methods described herein.

The method begins in step 1070, in which a contrast agent is introduced into the patient. The contrast agent may be introduced into the gastrointestinal tract, such as by swallowing, or by other routes, such as by injection. The contrast agent selectively accumulates in material of the type that the screening test is intended to detect, such as diseased tissue, and may accumulate there by binding to targeted molecules associated with such material. The contrast agent contains a fluorescent molecule, such as a dye. The spectral characteristics of lamp 840 are desirably matched to the absorption spectrum of the contrast agent. Preferably the passband of a filter 844 closely matches the emission spectrum of the contrast agent, so that the associated photodiode 846 is primarily responsive to fluorescence of the contrast agent. In a capsule 800 intended for screening tests using contrast agents, it may be possible to use only a single photodiode 846 and a single filter 844 having a passband that includes the contrast agent emission spectrum.

After contrast agent is introduced into the gastrointestinal tract in step 1070, the capsule 800 is introduced into the gastrointestinal tract in step 1000, and the process proceeds as described with respect to FIG. 3, with steps 1000-1060 corresponding to steps 300-360. An advantage of using a contrast agent is that the intensity of its fluorescence can be greater than the intensity of tissue autofluorescence, leading to more sensitive tests, and the contrast agent can be carefully tailored to bind to tissues of interest, leading to more specific tests.

The contrast agent may be a composite agent that includes several different components, each of which binds selectively to a different target material, and the different target materials can be of clinical significance to different gastrointestinal conditions of interest. Thus, a capsule 800 may be able to screen for multiple conditions in a single screening test. The different components of such a composite contrast agent may have fluorescent molecules having differing emission spectra, so that the conditions giving rise to an "abnormal" response in a screening test can be separately identified. In a capsule designed for use in such a screening test, it may be desirable to have one filter 844 and photodiode 846 for each component of the composite contrast agent, with each filter passband closely matching the emission spectrum of its corresponding contrast agent component.

An electronic capsule in accordance with this invention may include a memory that stores acquired data during the screening test. If the screening test gives an "abnormal" result, the stored data can be provided to a clinician to assist in further testing. To this end, after a test, the capsule may be retrieved and brought to the clinician, or the data may be downloaded from the capsule, such as by a wireless link. Such stored data may also be useful in comparing results of tests at different times.

Although this invention has been described with reference to particular embodiments, it will be appreciated that many variations will be resorted to without departing from the spirit and scope of this invention as set forth in the appended claims. The specification and drawings are accordingly to be regarded in an illustrative manner and are not intended to limit the scope of the appended claims.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function;
e) any of the disclosed elements may be comprised of hardware portions (e.g., including discrete and integrated electronic circuitry), software portions (e.g., computer programming), and any combination thereof;
f) hardware portions may be comprised of one or both of analog and digital portions;
g) any of the disclosed devices or portions thereof may be combined together or separated into further portions unless specifically stated otherwise; and
h) no specific sequence of acts is intended to be required unless specifically indicated.

The invention claimed is:

1. A method comprising:
    passing a swallowable, self-contained apparatus through a gastrointestinal tract, the self-contained apparatus comprising a discrete output generator;
    acquiring in the apparatus, during its passage through the gastrointestinal tract, data that is responsive to physical conditions adjacent the apparatus;
    generating, based on the acquired data, a discrete electrical signal relating to a condition of the gastrointestinal tract;
    determining that the apparatus has exited the GI tract; and
    generating, based at least in part on the generated electrical signal, at least in part on the determining that the apparatus has exited the GI tract and using the discrete output generator, a discrete output, wherein the discrete output is human perceptible at the apparatus after the apparatus exits the gastrointestinal tract.

2. The method of claim 1, wherein the human-perceptible output includes a color output.

3. The method of claim 2, wherein the color output is provided by releasing a colored substance from the apparatus.

4. The method of claim 1, wherein the human-perceptible output includes a light output.

5. The method of claim 1, wherein generating the discrete electrical signal includes comparing the acquired data with threshold data.

6. The method of claim 1, wherein a different discrete output state is provided for each possible state of the discrete electrical signal, and each discrete output state differs from the state of the apparatus prior to passing the apparatus through a gastrointestinal tract.

7. The method of claim 1, wherein the state of the discrete output indicates the presence, number, and/or location of abnormal conditions within the gastrointestinal tract.

8. The method of claim 1, further including introducing a contrast agent into tissues in the gastrointestinal tract prior to passing the apparatus through the gastrointestinal tract.

9. The method according to claim 1,
wherein the discrete output generator comprises a light generator, a color generator, or a sound generator and
wherein the discrete output is an emitted light at the capsule when the discrete output generator is a light generator, wherein the discrete output is a dispensed or changed color at the capsule when the discrete output generator is a color generator, and wherein the discrete output is an emitted sound at the capsule when the discrete output generator is a sound generator.

10. The method of claim 9, wherein the discrete output generator is a color generator and the causing the discrete output generator to generate a discrete output comprises opening a hatch on the apparatus to allow a colored material to exit the apparatus.

11. The method of claim 10, wherein the discrete output generator outputs a first discrete output when an abnormal condition of the gastrointestinal tract is detected and outputs a second discrete output in the absence of abnormal condition of the gastrointestinal tract.

12. A method comprising:
administering a swallowable, electronic capsule comprising a sensor and a discrete output generator to a patient such that the capsule passes through a gastrointestinal tract of the patient, wherein the capsule:
senses, using the sensor, a physical condition in the gastrointestinal tract; and
generates, using the discrete output generator and based on the sensed physical condition in the gastrointestinal tract, a discrete output that is human perceptible at the capsule after the capsule exits the gastrointestinal tract.

13. The method of claim 12, wherein the capsule generates a first discrete output when the physical condition is an abnormal condition of the gastrointestinal tract and generates a second discrete output when the physical condition is a normal condition.

14. The method of claim 12, wherein the discrete output indicates the presence, number, and/or location of an abnormal condition in the gastrointestinal tract.

15. The method of claim 12, wherein the human-perceptible output includes a color output.

16. The method of claim 12, wherein the color output is provided by releasing a colored substance from the capsule.

17. The method of claim 12, wherein the human-perceptible output includes a light output.

18. The method of claim 12, wherein the discrete output generator comprises a light generator, a color generator, or a sound generator, and
wherein the discrete output is an emitted light at the capsule when the discrete output generator is a light generator, wherein the discrete output is a dispensed or changed color at the capsule when the discrete output generator is a color generator, and wherein the discrete output is an emitted sound at the capsule when the discrete output generator is a sound generator.

19. The method of claim 18, wherein the discrete output generator is a color generator and the causing the discrete output generator to generate a discrete output comprises opening a hatch on the capsule to allow a colored material to exit the capsule.

20. The method of claim 19, wherein the discrete output generator outputs a first discrete output when an abnormal condition of the gastrointestinal tract is detected and outputs a second discrete output in the absence of abnormal condition of the gastrointestinal tract.

* * * * *